(12) United States Patent
Benicewicz et al.

(10) Patent No.: US 7,148,311 B2
(45) Date of Patent: Dec. 12, 2006

(54) LIQUID CRYSTAL POLYMERS

(75) Inventors: Brian Benicewicz, Loudonville, NY (US); Jiping Shao, Monroeville, PA (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 11/061,862

(22) Filed: Feb. 18, 2005

(65) Prior Publication Data

US 2005/0197483 A1    Sep. 8, 2005

Related U.S. Application Data

(63) Continuation of application No. PCT/US03/25910, filed on Aug. 19, 2003.

(60) Provisional application No. 60/404,487, filed on Aug. 19, 2002.

(51) Int. Cl.
   C08G 63/00    (2006.01)

(52) U.S. Cl. ............ 528/176; 252/299.01; 252/299.66; 528/193; 528/271

(58) Field of Classification Search ......... 252/299.01, 252/299.66; 528/176, 193, 271
   See application file for complete search history.

(56) References Cited

U.S. PATENT DOCUMENTS

| | | | |
|---|---|---|---|
| 4,219,461 A | 8/1980 | Calundann | 260/40 P |
| 4,395,513 A | 7/1983 | Calundann | 524/599 |
| 4,429,100 A | 1/1984 | Charbonneau et al. | 528/128 |
| 5,146,025 A | 9/1992 | Koyama et al. | 585/412 |
| 5,151,549 A | 9/1992 | Koyama et al. | 562/467 |
| 5,155,204 A | 10/1992 | Parodi et al. | 528/193 |
| 5,459,266 A | 10/1995 | Kvakovszky et al. | 544/336 |
| 5,851,423 A | 12/1998 | Teng et al. | 252/299.1 |
| 6,312,772 B1 | 11/2001 | Kuder et al. | 428/1.5 |
| 6,541,602 B1 | 4/2003 | Spreitzer et al. | 528/394 |
| 2002/0033474 A1* | 3/2002 | Tang et al. | 252/299.65 |

FOREIGN PATENT DOCUMENTS

EP    0 390 322 A2    2/2002

* cited by examiner

Primary Examiner—Terressa Boykin
(74) Attorney, Agent, or Firm—Heslin Rothenberg Farley & Mesiti P.C.

(57) ABSTRACT

Liquid crystal polyester derived from phenylene-naphthalene monomers and one or more comonomers display an improved balance of properties, including low melt viscosity, fast cycle time in molding, very low mold shrinkage, high tensile and/or flexural strength, solvent resistance, excellent barrier properties, low water absorption, low thermal expansion coefficient, excellent thermostability, and/or low flammability. The phenylene-naphthalene monomers are

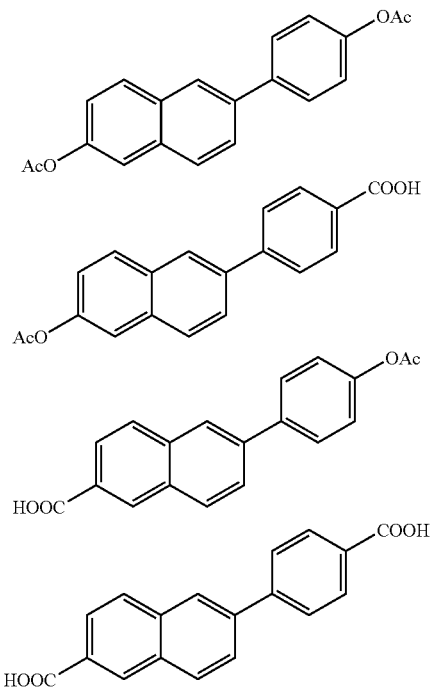

The one or more comonomers include 4-hydroxybenzoic acid, 2-hydroxy-6-naphthoic acid, terephthalic acid, isophthalic acid, and derivatives and combinations thereof.

18 Claims, No Drawings

LIQUID CRYSTAL POLYMERS

CROSS-REFERENCE TO RELATED APPLICATIONS

This application is a continuation of PCT/US03/25910, filed on Aug. 19, 2003, which claims priority from U.S. provisional application, Ser. No. 60/404,487, filed Aug. 19, 2002. The entire disclosure of both applications is incorporated herein by reference.

FIELD OF THE INVENTION

The invention relates to wholly aromatic liquid crystalline polymers.

BACKGROUND OF THE INVENTION

Liquid crystalline phases (mesophases) are partially ordered intermediate phases existing between the crystalline solid and isotropic liquid Materials in a liquid crystalline phase can flow like liquids, while retaining several features of crystalline solids such as optical and electromagnetic anisotropy characteristics. These properties are due to a specific amount of positional or orientational order in their structure. Mesogens or mesogenic groups are chemical moieties that induce mesophases under certain conditions. According to the ways to generate a liquid crystalline phase, these groups can be classified as lyotropic (exihibits liquid crystalline phase in solution) and thermotropic (exhibits liquid crystalline phase in melt, a single component system) liquid crystals.

The two main types of liquid crystalline phases are the nematic and smectic mesophases. In nematic phases the molecules have only an orientational order, while in smectic phases they have both orientational and positional order in one or more dimensions.

When a thermotropic LC compound is heated, the solid changes into a rather turbid liquid at the melting point. The fluidity may be high for a nematic phase and relatively low for the smectic phases. When observed between crossed polarizers under a microscope, the fluid is found to be strongly birefringent. Upon further heating, another transition point is reached where the turbid liquid becomes isotropic and consequently optically clear (clearing point). Between these two transition points, the liquid crystal phase is thermodynamically stable Both phase transitions are first order and the latent heat at the clearing point is usually an order of magnitude smaller than the melting point.

The polarizing m is a classical and useful tool for the study of liquid crystals. Dependent upon the boundary conditions and the type of LC phase, specific textures are observed and used to classify the different phases.

Liquid crystal polymers were discovered in the 1950s, when Onsager and Flory theoretically predicted that rigid rod-like macromolecules should display liquid crystalline properties. An axial ratio of 6.42 is enough for a polymer to form an LC melt. However, the molecular weight must be high to achieve good mechanical properties. The first main chain thermotropic liquid crystalline polymer was reported by Roviello and Sirigu in the 1970s, and since then many patents have been published and several LC polymers were commercialized.

Compared to monomer liquid crystals, polymer liquid crystals can display similar behaviors, and be classified into thermotropic and lyotropic LCPs. Several well known classes of polymers including polyesters, polyethers and polyamides can exhibit liquid crystalline phases. According to different mesogen positions in the polymer, LC polymers can be classified as main chain, side chain and combined liquid crystal polymers. More complex architectures are also possible.

LCPs are quite different from the conventional polymers. They have properties that include low melt viscosity, fast cycle time in molding, very low mold shrinkage, excellent mechanical properties, solvent resistance, excellent barrier properties, low water absorption, low thermal expansion coefficient, excellent thermostability, low flammability, etc. Therefore, they have been explored for numerous applications in the following areas: high-strength and high-modulus fibers, precision molded small components, films exhibiting excellent barrier properties, novel composites, processing aids in the melt, reversible information storage, electro-optical displays and non-linear optical devices.

The mesogenic groups in LCPs are usually rod-like or disk-like molecules, such as two or more rigid cyclic units. Aromatic rings are the most common units used in liquid crystal polymer to provide rigid rod structures. The synthesis, structure, rheology, processing, performance and applications of many LCPs have been comprehensively described in the literature, including Demus, D., et al, *Physical Properties of Liquid Crystals*; Wiley-VCH Verlag GmbH: Weinheim, 1999; Kwolek, S. L. *Encycl. Polym. Sci. Eng.* 1987, 9, 1–61; Collyer, A. A.; Editor. *Liquid Crystal Polymers. From Structures to Applications*; Elsevier: London, 1992; Ciferri, A.; Krigbaum, W. R.; Meyer, R. B.; Editor. *Polymer Liquid Crystals*; Academic Press: New York, N.Y., 1982; and Isayev, A. I.; Kyu, T.; Cheng, S. Z. D.; Editors. *Liquid-Crystalline Polymer Systems: Technological Advances*. (*Symposium at the 209th National Meeting of the American Chemical Society, Anaheim, Calif., Apr. 2–7,* 1995.) [In: *ACS Symp. Ser.,* 1996; 632]; ACS: Washington, D.C., 1996.

Thermotropic main chain liquid crystal polymers are the most important group of LCPs. They consist of mesogenic groups incorporated into the backbone of the polymer chain, and when prepared without flexible spacers, are usually known as wholly aromatic thermotropic LCPs. Because of their main chain stiffness and high packing density, they can exhibit excellent mechanical properties and are extremely useful in high-strength and high-modulus fibers. Since they form LC phases when melted, the viscosity in the melt state is relatively low, thus make the processing easy. Furthermore, the rod-like mesogenic groups can be aligned during the extruding or spinning process and give very high strength along the fiber direction.

Polyesters are a very important group of this class of polymers. Structures of some commercially important thermotropic copolyesters are listed in Table 1.

TABLE 1

Structures of some thermotropic co-polyesters

| # | Chemical Structure | Monomers |
|---|---|---|
| 1 | —[O—C₆H₄—CO]— | p-hydroxybenzoic acid (HBA) |
| 2 | —[O—C₆H₄—C₆H₄—O—CO—C₆H₄—CO]— | 4,4'-biphenol (BP)/ Terephthalic acid (TA) |
| 3 | —[O—naphthyl—CO]ₓ—[O—C₆H₄—CO]ᵧ— | 6-hydroxy-2-naphthoic acid (HNA)/HBA |
| 4 | —[O—C₆H₃(CH₃)—O—OC—C₆H₄—CO]— | 2-methyl hydroquinone (2-MHQ)/TA |
| 5 | —[CO—C₆H₄(meta)—CO]—[O—C₆H₄—CO]—[O—C₆H₄—C₆H₄—O]—[CO—C₆H₄—CO]— | Isophthalic acid (IA)/ HBA/BP/TA |

Generally, wholly aromatic thermotropic polyesters have poor solubility in normal organic solvents. Good solvents for this class of polymers include fluorinated compounds, such as pentafluorophenol (PFP), p-fluorophenol, trifluoroacetic acid, etc. Due to the poor solubility in common solvents, GPC data are usually not available in the literature. However, Kinugawa, et al. have investigated the molecular weight distributions of LC aromatic polyesters by the GPC-low-angle laser light scattering technique.

General characterization methods for this class of polymers include differential scanning calorimetry (DSC), polarized light microscopy, and wide-angle X-ray diffraction.

The ability to show anisotropy and readily induce orientation in the liquid crystalline state leads to materials with great strength in the direction of orientation, and thus, these polymers have received considerable attention as high-performance fibers, films and plastics, especially for injection molding applications.

The concept of a melt processable LC polymer is a natural extension of the discovery of KEVLAR® at DuPont, which is a wholly aromatic LC polyamide spun from concentrated sulfuric acid. Ekkcel I-2000 (copolyester from p-hydroxybenzoic acid (HBA), terephtalic acid (TA) and 4,4'-bisphenol (BP)) was the first melt spinable LC polyester reported in 1972. It has a melting point around 400° C., which is still too high for common melt spinning equipment.

In the 1970's and 1980's, aromatic LC polyesters were developed quickly and many LC polyesters were commercialized during this period. XYDAR® was first commercialized by Dartco Manufacturing Company in 1984 and was later manufactured by Amoco Chemical Company. It exhibits a melting point above 300° C. The VECTRA® family of LCPs was introduced by Celanese in 1985, with a melting point of 250–280° C.

Since these types of polymers offer a unique combination of properties, they are expected to offer potential solutions to problems which conventional materials are unable to solve. Currently, industrial activities are mainly concentrated on main chain thermotropic LCPs for injection molding applications.

Homopolymers from HBA or 6-hydroxy-2-naphthoic acid (HNA) exhibit high crystallinity and high melting point (higher than 600° C.). Although they provide excellent mechanical and thermal properties, their high melting points make them intractable and impractical for any commercial applications, since they are not melt spinnable or injection moldable. Thus, research has focused on developing new polyesters that have better tractability (lower melting point) without sacrificing other desirable properties.

The most common way to achieve this is to disrupt the regular chain structure. Until now, several methods were found to be effective in lowering the melting point of LC polyesters, such as the introduction of aliphatic spacer units on the backbone, using monomers with bent structures (kinks), ring substitution, "swivel" structures, and parallel-offset structures (crankshaft) into the backbone. However, a need for additional LCP having a desired balance of properties, including $T_g$, melting point ($T_m$), tensile strength and/or thermal stability, still exists.

Introducing aliphatic structures can give the backbone more flexibility, which disturbs the packing of the polymer chain and lowers the melting point. Numerous efforts have been made in the LC polyester area using this strategy. One example is X7G. By introducing the PET structure into the polymer, the melting point was lowered to about 230–300°

C. Another example is SIVERAS, an LC polyester based on PET, introduced by Toray Industries, Inc. in 1994. It is melt spinable at 310–320° C.

The major drawback for this strategy is that the aliphatic structure also decreases the degree of liquid crystallinity and lowers the thermal stability and mechanical properties dramatically. The properties are decreased in proportion with the length of the flexible spacer and its content in the polymer.

Instead of using para-substituted monomers, meta- or ortho-substitution on the phenyl ring will introduce a bent structure into the backbone, thus disturbing the packing and lowering the melting point. An example of this is Ekonol, which is composed of units derived from monomers HBA, TA, BP and a small amount of isophthalic acid (IA). The polymer exhibits very high tensile modulus and strength as a fiber. The problem with this strategy is that the kink structure can not exceed a specific amount in the total composition, without loss of LC properties. It was reported that for kink units having a 120' core angle such as isophthalic acid, the polymers will not exhibit liquid crystallinity with more than 60 mol % of kink units of the acids. For kink units having a 60' core angle, the maximum ratio is 30–40 mol %. As the amount of the kinking component increased, the liquid crystallinity and the orientability of the polyesters from the melt decreased. Therefore, the level of tensile and flexural properties decreased. Very high plastic and tensile properties were only possible when the kink component was less than 10 mol %.

Introducing a substituent in the aromatic ring can cause a decrease in crystallinity and hence a drop of the melting point of the polyester. The substituents, especially asymmetrical substituents, can disturb the packing of the chain by inter-chain separation and by the random arrangements called internal copolymerization effect.

Different substituents, including halogens (Cl and Br), methyl, phenyl, and phenoxy, have been investigated for their effects on lowering the melting point. The size, the additional degrees of rotational and conformational freedom of the substituent has a great effect on how much the melting point can be lowered. This approach can also result in complete loss of LC behavior. If the percentage of the substituent is too high, this may disturb the packing and the polymer may lose all LC properties in the melt.

The "swivel" structure is shown below. Since the two phenylene rings are not in the same plane, they are twisted at a small angle with respect to each other, and the packing density of the polymer is lowered. The linkage "X" can be a direct bond, S, O, etc. Since the disturbing influence is along the backbone axis, the risk of losing LC properties is normally high, except in the case of a direct bond. This is due in part to the "kink" which is imparted by the O or S bond.

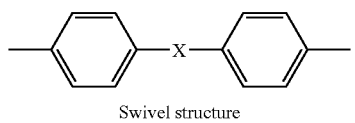

Swivel structure

The simplest "swivel" structure is biphenol (BP), in which there is a direct linkage between the two rings. The liquid crystallinity of the polymers will not be completely lost even at 100 mol % of BP of the diols. The small twist angle of BP does have an effect on lowering the melting point. For example, Ekkcel I-2000 in which BP is one of the co-monomers, the melting point is more than 200° C. lower than homopolymer of HBA.

The common monomer used in this strategy is 6-hydroxy-2-naphthoic acid (HNA). The 2,6-naphthalene ring structure introduces a crankshaft structure in the polymer chain. After this modification, the melting points are lowered without sacrificing significant crystallinity since the backbone is still parallel to the original axis. Therefore, the LC properties and mechanical properties can be maintained even with a relatively high percentage of HNA monomer.

One of the most prominent high performance LCP polyesters developed was VECTRA®, derived from HNA and HBA. It is melt processable with common processing equipment capable of handling materials with melting points at 250–280° C. The excellent properties of VECTRA® polymers make them useful in a variety of applications such as optical fiber cables, fishing line and high strength fiber reinforced composites, etc.

From the discussion above, we can see that the introduction of "swivel" and "crankshaft" structures into the backbone of LC polymers are two of the best strategies to achieve low melting point for main chain LC polyester while maintaining excellent mechanical and thermal properties. Therefore, in order to obtain even better tractability and excellent mechanical properties, and investigate their structure-property relationships, wholly aromatic LC polyesters containing a phenylene-naphthalene structure would be desirable.

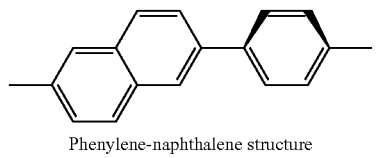

Phenylene-naphthalene structure

Although some compounds containing the phenylene-naphthalene structure have been reported, no polymers containing this subunit have been described in the scientific or patent literature. 2-(4-Hydroxyphenyl)naphthalene-6-carboxylic acid is disclosed in U.S. Pat. Nos. 5,151,549 and 5,146,025, but no description of any polymers prepare from the monomer appear in either patent.

Phenylene-naphthalene monomers are useful monomers for themotropic LC polyesters, as they may introduce additional dissymmetry into their monomers and polymers, combine the "crankshaft" and "swivel" effects together, and maintain wholly aromatic backbone structure. Therefore, better tractability can be achieved without sacrificing mechanical and liquid crystal properties.

SUMMARY OF THE INVENTION

It has been unexpectedly discovered that wholly aromatic thermotropic LC polyesters containing the phenylene-naphthalene moiety may be prepared from monomers of formula:

A-A monomer

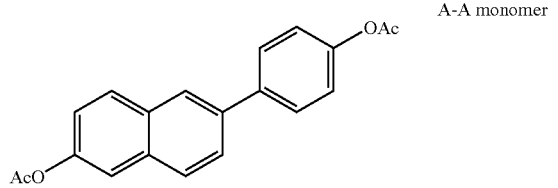

A-B monomer

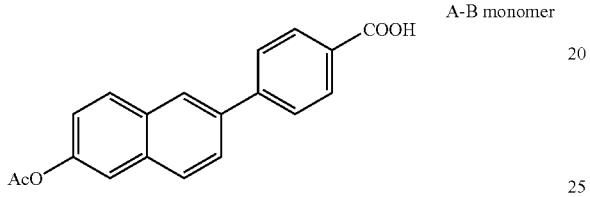

B-A monomer

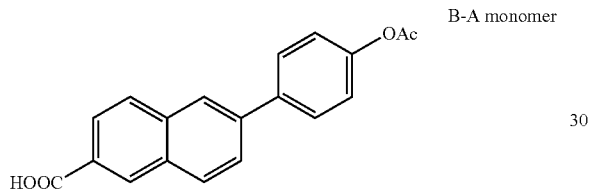

B-B monomer

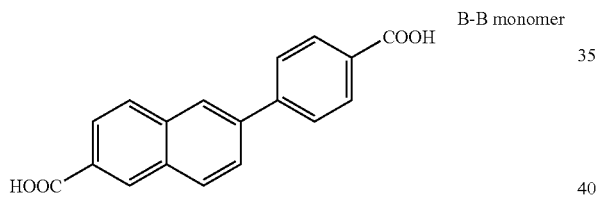

Copolyesters from these monomers exhibit superior physical and mechanical properties, including low melt temperatures.

DETAILED DESCRIPTION OF THE INVENTION

The wholly aromatic thermotropic LC polyesters of the present invention are composed of structural or repeating units of formula I, II, III, and/or IV.

I

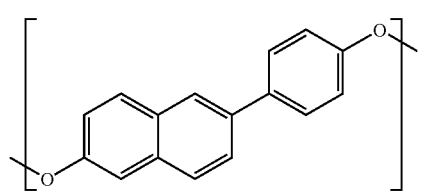

II

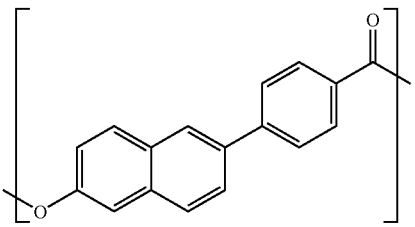

III

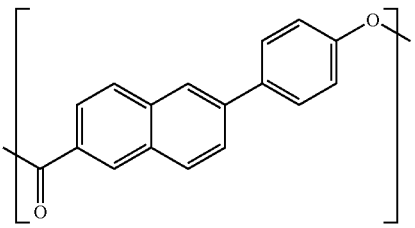

IV

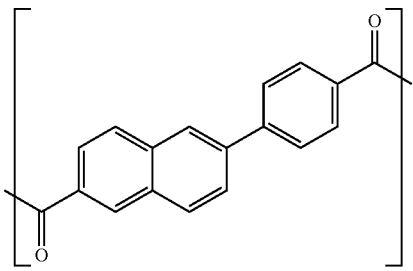

The repeating units may be derived from any monomer having the phenylene-naphthalene structure and appropriate substituents, including COOH/OAc, COOPh/OH, and COOCH$_3$/OAc. Acid/alcohol (COOH/OH) substituents are not considered appropriate, as reaction rates of such monomers are relatively low, and polymerization may result in a product that is contaminated with water. Particularly useful monomers are shown below. These are designated A-A, A-B, B-A and B-B, according to the acetoxy and carboxy substituents on the naphthalene and phenyl rings, respectively.

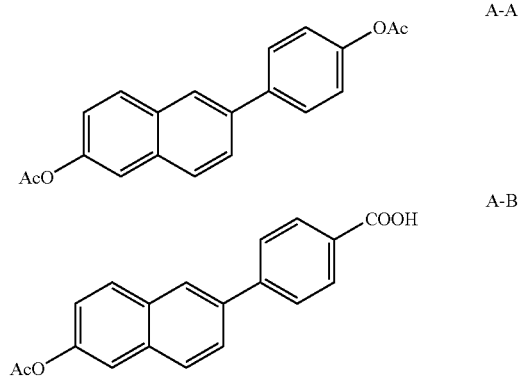

-continued

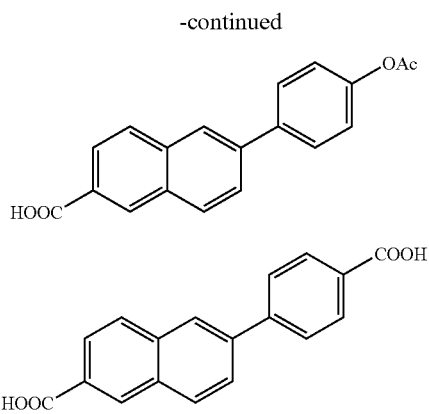

B-A

B-B

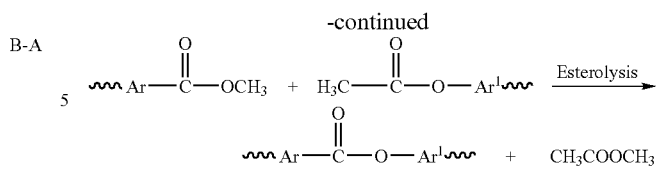

The LC polyesters may include repeating units in addition to those above, including those derived from monomers such as 4-hydroxybenzoic acid, 2-hydroxy-6-naphthoic acid, 4-aminobenzoic acid, 4-carboxy-4' hydroxy-1,1'-biphenyl, terephthalic acid, isophthalic acid, phthalic acid, 2-phenylterephthalic acid, 1,2-naphthalene dicarboxylic acid, 1,4-naphthalenedicarboxylic acid, 2,6-naphthalene dicarboxylic acid and 4,4'-biphenyldicarboxylic acid or derivatives such as acetates or esters thereof. 4-Hydroxybenzoic acid, 2-hydroxy-6-naphthoic acid, terephthalic acid, and isophthalic acid are preferred comonomers. The LC polymers may also include end units derived from compounds such as resorcinol, hydroquinone, methyl hydroquinone, phenyl hydroquinone, catechol, 4,4'-dihydroxybiphenyl, and/or acetaminophen.

The LC polyesters may be prepared by any suitable condensation or step-growth polymerization process; however, melt polycondensation is a preferred method. Industrial processes for LC polymerization typically do not utilize direct esterification between diacid and diol monomers, because reaction rates can be slow, and it can be difficult to remove water completely, as noted above. Accordingly, preferred methods for the synthesis of LC polyesters are alcoholysis, esterolysis, acidolysis and phenolysis, as depicted in Scheme 1. The acidolysis method is used for the manufacture of many commercial main-chain LCPs. Acetic acid is released as the by-product.

In the phenolysis process, the phenyl ester of the aromatic acid is used instead of the aromatic acid. This reaction eliminates phenol as the by-product. Compared with acidolysis, the rate of the phenol formation is relatively slow, and it is more difficult to remove phenol than acetic acid. In the esterolysis method the acetate esters are used and methylacetate is the by-product. Alcoholysis uses readily available starting materials. Its by-product, methanol, is relatively non-toxic and easy to remove.

The polymerization may also be carried out in solution. High boiling solvents, such as Aroclor-7133, Therminol-66 and Marlotherm-S may be used as heat transfer fluids to carry out the transesterification reactions. This method can eliminate certain side reactions that may occur in melt polycondensation reaction. However, it may also change the morphology and/or thermal transition of the products. The polymers obtained from this method typically yield lower number- and weight-average molecular weights than those from the melt polycondensation reaction.

For the acidolysis method, diacetate derivatives of the aromatic diol and/or acetoxy derivatives of the aromatic acids are reacted with aromatic dicarboxylic acids in the melt. The polymerization temperature is typically between 250° C. and 300° C., depending on different monomers. The condensation by-product in this reaction is acetic acid and is usually removed by distillation, then vacuumed at high temperature during the final stage of the polymerization. Catalysts for the reaction include acetates of sodium, potassium, magnesium, zinc, manganese, cobalt, and antimony (III) oxide.

In one embodiment, the present invention relates to a process for preparing a liquid crystal polymer. The process includes polymerizing one or more phenylene-naphthalene monomers selected from the group consisting of

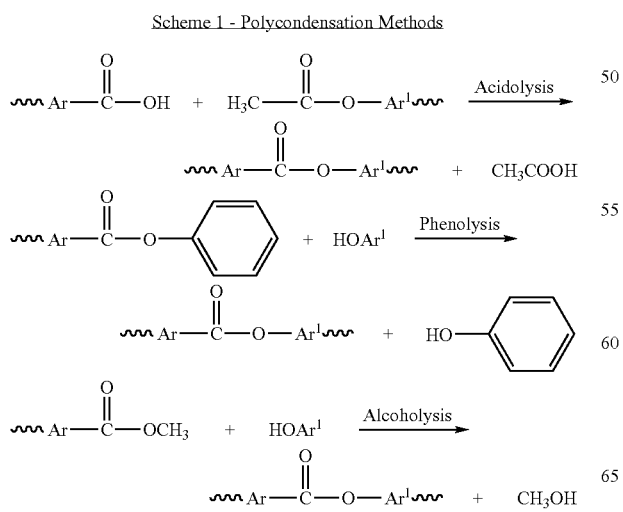

Scheme 1 - Polycondensation Methods

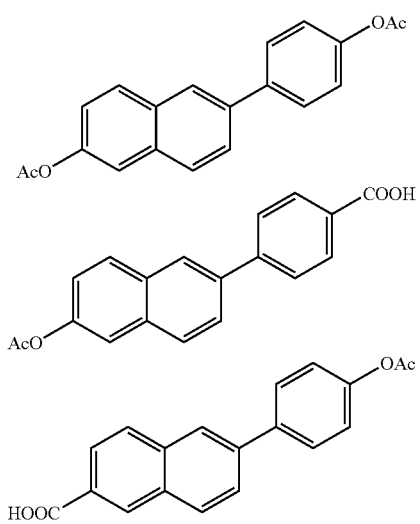

-continued and combinations thereof, and, optionally, one or more comonomers. The one or more comonomers may be 4-hydroxybenzoic acid, 2-hydroxy-6-naphthoic acid, terephthalic acid, isophthalic acid, hydroquinone, derivatives thereof or a combination thereof.

Monomers containing the phenylene-naphthalene structure may be synthesized by a Suzuki cross-coupling reaction, as shown in Scheme 2.

SCHEME 2

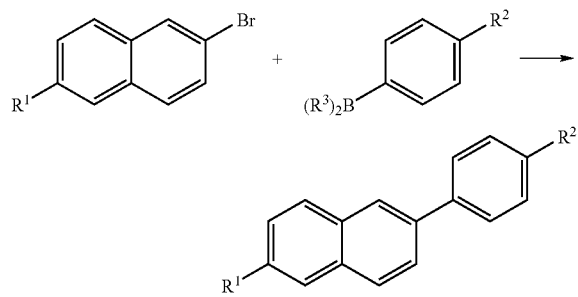

wherein $R^1$ and $R^2$ are independently carboxy, acyloxy, or hydroxy; and $R^3$ is hydroxy, alkoxy or aryl.

A preferred embodiment of this process is shown in Scheme 2A

SCHEME 2A

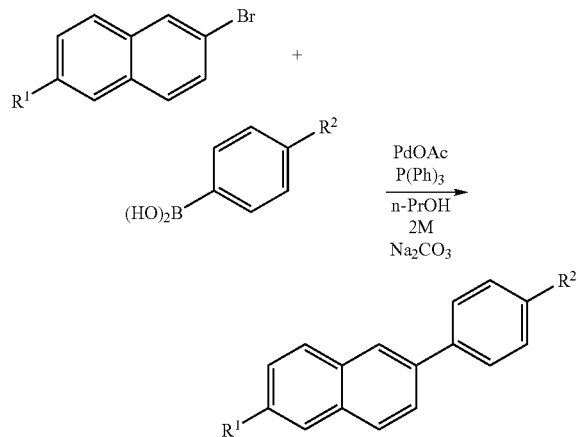

wherein $R^1$ and $R^2$ are independently carboxy, acyloxy, or hydroxy; and $R^3$ is hydroxy, alkoxy or aryl. In particular, $R^1$ and $R^2$ may be carboxy and acetoxy, respectively, both acetoxy, or both carboxy.

Boronic acids are the common substrates in this reaction, along with aryl halides or triflates. Esters of boronic acids and arylboranes are also used. The most commonly used catalyst is tetrakis(triphenylphosphine) palladium(0). Other palladium catalysts have also been employed with success. This reaction requires bases during the coupling, and the best results are achieved with the use of a relatively weak base such as sodium carbonate. Other bases such as sodium hydrogen carbonate, triethylamine and thallium hydroxide are also effective. The suggested mechanism by Suzuki for this reaction is as follows: First, an oxidative addition of the catalyst to the aryl halide gives an intermediate Ar[Pd]X. Secondly, a transmetallation step yields a diarylated palladium moiety. Finally a reductive elimination from the diarylated palladium compound gives the biaryl product and the palladium(0) catalyst re-enters the catalytic cycle The LC polymers of the present invention are useful as high-strength and high-modulus fibers, and as high-performance films and plastics, especially for injection molding applications.

EXPERIMENTAL

Material and Instruments

4-Methoxybenzene boronic acid and 4-carboxyphenyl boronic acid were purchased from Lancaster and Frontier Scientific, Inc. 2-Bromo-6-methoxynaphthalene was purchased from Lancaster and Aldrich. Triphenylphosphine (99%) was purchased from Lancaster. 1-Propanol, pentanone, acetic anhydride, palladium acetate and hydrobromic acid (48% water solution) were purchased from ACROS. All materials were used as received without purification.

Proton nuclear magnetic resonance spectra ($^1$H NMR) were recorded on a Varian 500 spectrometer and referenced with respect to residual solvent. Elemental analyses were carried out by Midwest Microlab, LLC, Indianapolis, Ind. 46250. GC-MS spectra were obtained by Shimadzu GCMS-QP5000 gas chromatograph mass spectrometer. IR spectra were obtained from a Bio-Rad FTS 3000MX Mid-IR Excalibur spectrometer. Melting points were measured in capillary with a Mel-Temp apparatus and the thermometer was not calibrated. Thermogravimetric analysis (TGA) tests were carried out on a Perkin-Elmer TGA 7 with $N_2$ purging at a heating rate of 20° C./min. Differential scanning calorimetry (DSC) tests were carried out on a Perkin-Elmer DSC 7 and a TA Instruments DSC 2920 with $N_2$ purging at a heating rate of 10° C./min. Melting points were recorded as peak temperatures. The liquid crystalline behavior of the compounds was studied using polarized microscopy (Nikon Eclipse E600) with crossed polarizers, equipped with a heating stage (Linkam THMS-600). The magnification used was normally 100 or 200×.

Synthesis of
2-methoxy-6-(4'-methoxyphenyl)naphthalene
(DMPN)

In an 100 mL three-necked RB flask equipped with a magnetic bar, a condenser and a nitrogen gas inlet, 2-bromo-6-methoxynaphthalene (7.32 g, 30 mmol), 4-methoxybenzene boronic acid (4.86 g, 32 mmol) and 1-propanol (50 mL) were mixed and stirred at room temperature for approx. 30 min. Palladium acetate (0.02 g, 0.09 mmol), triphenylphosphine (0.07 g, 0.27 mmol), $Na_2CO_3$ solution (2M, 18 mL, 36 mmol) and water (10 mL) were added and the mixture was refluxed for 1.5 h. When the mixture was still hot, 30 mL of water was added and the mixture was stirred and cooled to room temperature. The resultant crystals were filtered, washed with water and recrystallized from acetone to give the DMPN title compound as colorless flakes (6.86 g, 86%). mp 194–196° C. (DSC 196° C). $^1$H NMR (500 MHz, CDCl$_3$) δ 3.88 (s, 3H), 3.95 (s, 3H), 7–8 (m, 10 H). IR (KBr) ν (cm$^{-1}$): 3058 (Ph-H, w), 1028 (OCH$_3$, s). Anal. Calcd for C$_{18}$H$_{16}$O$_2$: C, 81.79; H, 6.10. Found: C, 81.80; H, 6.25. GC-MS (m/z) 264 (M$^+$).

Synthesis of
2-acetoxy-6-(4'-acetoxyphenyl)naphthalene (DAPN)

A mixture of DMPN (2.54 g, 10 mmol), hydrobromic acid (48% water solution, 40 mL) and acetic acid (40 mL) was purged with nitrogen and refluxed overnight. The mixture was poured into 200 mL of water and the resultant solid was filtered and dried. 2-Hydroxy-6-(4'-hydroxyphenyl)naphthalene was obtained as a light purple solid (2.20 g, 96%). The crude intermediate was stirred with 40 mL of acetic anhydride and 1–2 drops of sulfuric acid for 2 hours. The resultant pink solid was filtered and recrystallized from acetone to afford the title compound as light yellow crystals (2.75 g, 90%). mp 178–180° C. (solid-turbid liquid), 205–206° C. (clear point); DSC 182° C. and 207° C. $^1$H NMR (500 MHz, CDCl$_3$) δ 2.29 (s, 3H), 2.33 (s, 3H), 7.2–8.3 (m, 10H). IR (KBr) ν (cm$^{-1}$): 1755 (C=O, s), 1368 (CH$_3$CO, s), 1200–1249 (O—C—O, s). Anal. Calcd for C$_{20}$H$_{16}$O$_4$: C, 74.99; H, 5.03. Found: C, 74.88; H, 5.02. GC-MS (m/z) 320 (M$^+$).

Synthesis of
2-(4'-carboxyphenyl)-6-methoxynaphthalene (CMPN)

In an 100 mL three-necked RB flask equipped with a magnetic bar, a condenser and a nitrogen gas inlet, 2-bromo-6-methoxynaphthalene (4.74 g, 20 mmol), 4-carboxybenzene boronic acid (3.50 g, 20 mmol) and 1-propanol (40 mL) were mixed and stirred at room temperature for approximately 30 min. Palladium acetate (0.014 g, 0.003 equiv., 0.06 mmol), triphenylphosphine (0.047 g, 0.009 equiv., 0.18 mmol), Na$_2$CO$_3$ solution (2M, 12 mL, 1.20 equiv., 24 mmol) and water (8 mL) were added and the mixture was refluxed for 1.5 h. When the mixture was still hot, 25 mL of water was added and the mixture was stirred and cooled to room temperature. The resultant crystals were filtered, washed with water and refluxed with 50 mL of acetic acid for 3–4 h. A white solid was obtained (5.08 g) and recrystallization from acetone showed the title compound as white crystals (4.63 g, 83%). mp 288–289° C. $^1$H NMR (500 MHz, DMSO) δ 3.90 (s, 3H), 7.2–8.3 (m, 10H), 12.99 (s, 1H). IR (KBr) ν (cm$^{-1}$): 2500–3000 (COO—H, very broad, m), 1030 (OCH$_3$, s), 1678 (C=O, s). Anal. Calcd for C$_{18}$H$_{14}$O$_3$: C, 77.68; H, 5.07. Found: C, 77.56; H, 5.08.

Synthesis of
2-(4'-carboxyphenyl)-6-acetoxynaphthalene (CAPN)

A mixture of CMPN (2.78 g, 10 mmol), hydrobromic acid (48% water solution, 80 mL) and acetic acid (150 mL) was purged with nitrogen and refluxed for 48 hours. The mixture was then poured into 400 mL of water and the resultant purple solid was filtered and dried (2.58 g, 98%). The crude intermediate was stirred with 40 mL of acetic anhydride and 1–2 drops of sulfuric acid for 2 hours. The resultant solid was filtered (2.88 g) and recrystalization from acetone or pentanone afforded the title compound as light yellow crystals (2.02 g, 66%). mp 254–256° C. (DSC 262° C.). $^1$H NMR (500 MHz, DMSO) δ 2.34 (s, 3H), 7.3–8.4 (m, 10H), 13.02 (s, 1H). IR (KBr) ν (cm$^{-1}$): COO—H (2800–3100, broad, m), 1685 (C=O, s), 1225 (C—O—C, vs), 1365 (CH$_3$CO, s). Anal. Calcd for C$_{19}$H$_{14}$O$_4$: C, 74.50; H, 4.61. Found: C, 74.28; H, 4.59.

Synthesis of 6-(4'methoxyphenyl)-2-naphthoic acid (MCPN)

In an 100 mL three-necked RB flask equipped with a magnetic bar, a condenser, and a nitrogen gas inlet, 6-bromo-2-naphthoic acid (2.62 g, 96%, 10 mmol), 4-methoxy-benzeneboronic acid (1.52 g, 10 mmol) and 1-propanol (20 mL) were mixed and stirred at room temperature for about 30 min. Palladium acetate (0.007 g, 0.003 equiv., 0.03 mmol), triphenylphosphine (0.024 g, 0.009 equiv., 0.9 mmol), Na$_2$CO$_3$ solution (2 M, 8 mL, 1.20 equiv., 12 mmol) and water (4 mL) were added and the mixture was refluxed for 2 h. When the mixture was still hot, 20 mL of water was added and the mixture was stirred and cooled to room temperature. The resultant crystals were filtered, washed with water and refluxed with 50 mL of acetic acid for 3–4 h. A white solid was obtained (2.55 g) and recrystallization from acetone gave the title compound as white crystals (2.24 g, 81%): mp 267–269° C.

$^1$H NMR (500 MHz, DMSO) δ 3.83 (s, 3H), 7.0–8.6 (m, 10H), 13.03 (s, 1H). IR (KBr) ν (cm$^{-1}$): 2800–3100 (Ph-COO—H, broad, m), 1690 (C=O, s), 1034 (OCH$_3$, s). Anal. Calcd for C$_{18}$H$_{14}$O$_3$: C, 77.68; H, 5.07. Found: C, 77.41; H, 5.02.

Synthesis of 6-(4'-acetoxyphenyl)-2-naphthoic acid (ACPN)

A mixture of MCPN (2.78 g, 10 mmol), hydrobromic acid (48% water solution, 80 mL) and acetic acid (150 mL) was purged with nitrogen and refluxed for 48 hrs. The mixture was then poured into 400 mL of water and the resultant purple solid was filtered and dried (2.53 g, 96%). The crude intermediate was stirred with 40 mL of acetic anhydride and 1–2 drops of sulfuric acid for 2 hours. The resultant solid was filtered (2.91 g) and recrystallization from acetone or pentanone afforded the title compound as light yellow crystals (2.18 g, 71%). mp 256–258° C. (DSC 260° C.). $^1$H NMR (500 MHz, DMSO) δ 2.31 (s, 3H), 7.2–8.7 (m, 10H), 13.1 (s, 1H). IR (KBr) ν (cm$^{-1}$): 2800–3100 (PhCOO—H, broad, m), 1686 (C=O, s), 1364 (CH$_3$CO, s). Anal. Calcd for C$_{19}$H$_{14}$O$_4$: C, 74.50; H, 4.61. Found: C, 74.53; H, 4.59.

Synthesis of
2-carboxy-6-(4'-carboxyphenyl)naphthalene (DCPN)

In an 100 mL three-necked RB flask equipped with a magnetic bar, a condenser and a nitrogen gas inlet, 6-bromo-2-naphthoic acid (2.51 g, 10 mmol), 4-carboxybenzene boronic acid (1.66 g, 10 mmol) and 20 mL of 1-propanol were mixed and stirred at room temperature for about 30 min. Palladium acetate (0.007 g, 0.003 equiv., 0.03 mmol), triphenylphosphine (0.024 g, 0.009 equiv., 0.9 mmol), Na$_2$CO$_3$ solution (2 M, 8 mL, 1.20 equiv., 12 mmol) and water (4 mL) were added and the mixture was refluxed for 1.5 h. When the mixture was still hot, 20 mL of water was added and the mixture was stirred and cooled to room temperature. The solid was separated by filtration and refluxed with 2 mL of 1M HCl and 25 mL of acetic acid. A white solid was obtained after filtration. No melting point was detected up to 350° C. $^1$H NMR (500 MHz, DMSO) δ 7.9–8.7 (m, 10H), 13.1 (s, 2H). IR (KBr) ν (cm$^{-1}$): Anal. Calcd for $C_{18}H_{12}O_4$: C, 73.97; H, 4.14. Found: C, 73.59; H, 4.05.

Suzuki Coupling Reactions

The reaction conditions of Huff et al.(*Org. Synth.* 1988, 75, 53–60) were used in our coupling reactions. The reactions were carried out in 1-propanol and water. Sodium carbonate was used as the base, and triphenylphosphine and palladium acetate were used to generate Pd(0) in situ. The temperature was around 100° C. for refluxing. Typically, reactions were completed within one hour. The solution was dark red-orange in color at the end of the reaction and the products were precipitated from the solution even at refluxing temperature. After cooling to room temperature, the mixture was filtered and washed with water to give crystals or powders. For compounds containing an acid group, the resultant products were sodium salts of the acid. Acidification with acetic acid gave the acid products. The results are summarized in Table 2.

An easy and common way to cleave the aryl methyl ether group is by refluxing the substrates overnight in hydrobromic acid solution. This method worked well for the A-A monomer (Scheme 3). For A-B or B-A monomers, the solubilities are much lower than the A-A monomer and extended reaction times (24–48 hours) were required to complete the demethylation process. From the NMR spectra, the uncleaved compound was less than 3% in the crude product. The yields were very good (above 95%). These cleaved compounds were used in the next step after workup without further purification.

Scheme 3

Synthesis of Monomers: Suzuki coupling

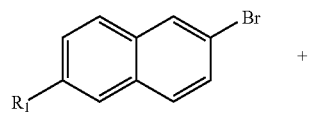

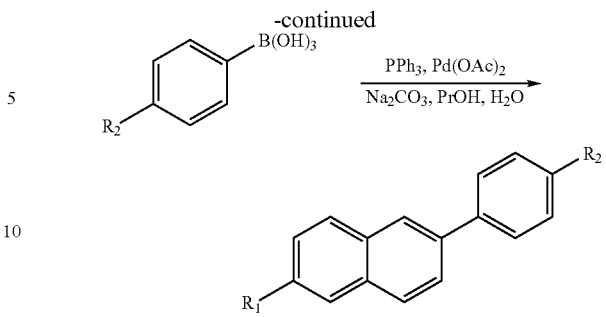

TABLE 2

|  | A—A | A-B | B-A | B—B |
| --- | --- | --- | --- | --- |
| $R_1$ | OMe | OMe | COOH | COOH |
| $R_2$ | OMe | COOH | OMe | COOH |
| Yield *(%) | 85–90 | 80–85 | 80–85 | 75–80 |

*Isolated yield after recrystallization

The acetylation reaction was carried out in acetic anhydride with sulfuric acid as catalyst. The reactions were performed at room temperature or at 40–50° C. for 2–3 hours. The yields were nearly quantitative.

The resultant products were usually pink powders, and recrystallization gave fine, light yellow or pink crystals. The structures of pure products were confirmed by NMR, IR, GC-MS and elemental analysis. For the A-A monomer, the GC-MS showed a molecular ion peak with m/z=320 (EI), which matched the calculated molecular weight of the molecule.

Almost all the monomers and intermediates showed liquid crystal phases when heated. The liquid crystal properties were investigated by capillary melting test, DSC and cross polarized microscope. Transition temperatures were determined by the peak temperatures from DSC curves. The data is listed in Table 3 (Cr=crystal, N=nematic, I=isotropic liquid).

TABLE 3

Structures and transition temperature for monomers

| Sample ID | Structures | Transition Temperature |
| --- | --- | --- |
| Shao-01-01 | (MeO–naphthalene–C6H4–OMe) | Cr 196 I(I 187 N 142 Cr) |
| Shao-01-06 | (MeO–naphthalene–C6H4–COOH) | Cr 288 N 338 I |

TABLE 3-continued

Structures and transition temperature for monomers

| Sample ID | Structures | Transition Temperature |
|---|---|---|
| Shao-02-27 | 6-hydroxy-naphthalene-2-yl with 4-COOH phenyl | Cr 296 N 322 I |
| Shao-01-10 | 6-carboxy-naphthalene-2-yl with 4-OMe phenyl | Cr 269 N 339 I |
| Shao-01-46 | 6-carboxy-naphthalene-2-yl with 4-OH phenyl | Cr 316 N 416 I |
| Shao-01-21 | 6-acetoxy-naphthalene-2-yl with 4-OAc phenyl | Cr 182 N 207 I |
| Shao-01-18 | 6-hydroxy-naphthalene-2-yl with 4-OH phenyl | Cr 270 I |
| Shao-01-54 | 6-acetoxy-naphthalene-2-yl with 4-COOH phenyl | Cr 263 N→polymerization |
| Shao-01-63 | 6-carboxy-naphthalene-2-yl with 4-OAc phenyl | Cr 260 N→polymerization |
| Shao-01-16 | 6-carboxy-naphthalene-2-yl with 4-COOH phenyl | No melting point was detected up to 350° C. |

2-methoxy-6-(4'-methyoxyphenyl)naphthalene (Shao-01-01) did not show any liquid crystal phase during heating process, however nematic phase was observed during cooling (monotropic liquid crystalline phase). The A-A monomer (Shao-01-21) melted at around 180° C. into a turbid liquid (nematic liquid crystal phase), and turned into a clear liquid at 206° C. A-B and B-A monomers (Shao-01-54 and Shao-01-63) melted to nematic phase, however the clearing point was not observed up to decomposition temperature because the polymerization occurs at higher temperatures. The B-B monomer's melting point was very high and was not observed up to 350° C. However, under fast heating rate (40° C./min), an endothermal peak was observed on the DSC curve at around 420° C., which is quite above its decomposition temperature.

Some of the DSC curves of the monomers showed two endothermal transition peaks when heated. The enthalpies for the second peaks (clearing points) were much smaller than that for the first peaks (melting points).

Under polarized light microscope, threaded textures were commonly observed when the monomers melted. These textures are typical textures for nematic liquid crystalline phases.

The thermal stability of all monomers was investigated by TGA at a heating rate of 20° C./min under $N_2$ atmosphere. The temperature at 5% and 10% weight loss were used to characterize the thermal stability and the results are summarized in Table 4.

TABLE 4

| | TGA data of monomers | |
|---|---|---|
| Sample ID | 5% weight loss temperature (° C.) | 10% weight loss temperature (° C.) |
| Shao-01-01 | 182 | 199 |
| Shao-01-06 | 220 | 233 |
| Shao-01-10 | 253 | 270 |
| Shao-01-21 | 195 | 208 |
| Shao-01-54 | 230 | 250 |
| Shao-01-63 | 240 | 257 |

The entropy and enthalpy changes at transition temperatures (at Tg and Tm) are measured or calculated from DSC curves and listed in Table 5.

TABLE 5

Entropy and enthalpy at transitions for monomers

| ID | Structures | At Melting Point (J/g) | At Clearing Point (J/g) |
|---|---|---|---|
| Shao-01-01 | [MeO-naphthalene-C6H4-OMe] | ΔH = 130.2<br>ΔS = 0.28 | N/A |
| Shao-01-06 | [MeO-naphthalene-C6H4-COOH] | ΔH = 113.8<br>ΔS = 0.20 | ΔH = 26.2<br>ΔS = 43 × 10$^{-3}$ |
| Shao-01-27 | [HO-naphthalene-C6H4-COOH] | ΔH = 84.7<br>ΔS = 0.15 | ΔH = 4.8<br>ΔS = 8.1 × 10$^{-3}$ |
| Shao-01-10 | [HOOC-naphthalene-C6H4-OMe] | ΔH = 102.8<br>ΔS = 0.19 | ΔH = 19.0<br>ΔS = 31 × 10$^{-3}$ |

TABLE 5-continued

Entropy and enthalpy at transitions for monomers

| ID | Structures | At Melting Point (J/g) | At Clearing Point (J/g) |
|---|---|---|---|
| Shao-01-46 | HOOC–naphthalene–C6H4–OH | ΔH = 96.8<br>ΔS = 0.16 | ΔH = 2.1<br>ΔS = 3.0 × 10$^{-3}$ |
| Shao-01-21 | AcO–naphthalene–C6H4–OAc | ΔH = 111.7<br>ΔS = 0.22 | ΔH = 3.5<br>ΔS = 7.5 × 10$^{-3}$ |
| Shao-01-18 | HO–naphthalene–C6H4–OH | ΔH = 100.8<br>ΔS = 0.19 | N/A |
| Shao-01-54 | AcO–naphthalene–C6H4–COOH | ΔH = 87.7<br>ΔS = 0.16 | N/A |
| Shao-01-63 | HOOC–naphthalene–C6H4–OAc | ΔH = 72.1<br>ΔS = 0.13 | N/A |

Compared to other monomers with the same functional groups but different core structure, we can see that as the rigid rod length increases, the LC temperature range also increases (Table 6 and Table 7). An interesting point is that CMPN and MCPN have almost the same clearing temperature (338 and 339° C.), indicating that the LC phase stabilities are almost the same for these two compounds. However, the melting point of MCPN is nearly 20 degrees lower than CMPN.

TABLE 6

Transition temperatures for some monomers

| Monomers | Structures | Transition Temperatures (° C.) |
|---|---|---|
| 6-methoxy-2-naphthoic acid | MeO–naphthalene–COOH | Cr 206 N 219 I |
| 4'-methoxy-4-carboxybiphenyl | MeO–C6H4–C6H4–COOH | Cr 258 N 300 I |

TABLE 6-continued

Transition temperatures for some monomers

| Monomers | Structures | Transition Temperatures (° C.) |
|---|---|---|
| 2-(4'carboxyphenyl)-6-methoxy naphthalene (CMPN) | MeO-naphthalene-C6H4-COOH | Cr 288 N 338 I |
| 6-(4'-carboxyphenyl)-2-naphthoic acid (MCPN) | HOOC-naphthalene-C6H4-OMe | Cr 269 N 339 I |

For the diacetoxy compounds in Table 7, the similar effect was observed. When the core structures are naphthalene and biphenyl, the molecules do not show any liquid crystalline behavior. The phenylene-naphthalene structure monomer began to show nematic phase by providing longer rigid rod length. However, when compared to symmetric monomer 6,6'-diacetoxy-2,2'-bianphthyl, both the melting point and clearing point of dissymmetric phenylene-naphthalene monomer were much lower.

(PFP) and pentafluorobenzene (PFB) were purchased from Acros. Tetrachloroethylene (TCE) was purchased from Aldrich. 2-acetoxy-6-naphthoic acid (ANA), 4-acetoxy benzoic acid (ABA) were purchased from Proctor. Benzoic acid was purchased from Fisher. 6-Acetoxy-2-naphthoic acid (ANA), 4-acetoxybenzoic acid (ABA) were purchased from Proctor. Terephthalic acid (TA) was purchased from Amoco. A heat transfer fluid, Therminol 66, was obtained from Solutia, Inc.

TABLE 7

Transition temperatures for some monomers

| Monomers | Structures | Transition Temperatures (° C.) |
|---|---|---|
| 2,6-diacetoxynaphthalene | AcO-naphthalene-OAc | Cr 175 I |
| 4,4'-diacetoxybiphenyl | AcO-C6H4-C6H4-OAc | Cr 161 I |
| 2-acetoxy-6-(4'-acetoxyphenyl)naphthalene (DAPN) | AcO-naphthalene-C6H4-OAc | Cr 182 N 207 I |
| 6,6'-diacetoxy-2,2'-binaphthyl | AcO-naphthalene-naphthalene-OAc | Cr 246 N 304 I |

Materials and Instruments—Synthesis of Polymers

Potassium acetate (KOAc), tin (II) trifluoromethane sulfonate ((CF$_3$SO$_3$)$_2$Sn), phenyl acetate, pentafluorophenol The dispersing agent, Ganex V-220, was obtained from ISP Tehnologies, Inc. All materials were used as received without purification.

GC-MS spectra were obtained on a Shimadzu GCMS-QP5000 gas chromatograph mass spectrometer. TGA tests were carried out on a Perkin-Elmer TGA 7 with $N_2$ purging at heating rate of 20° C./min. DSC tests were carried out on a Perkin-Elmer DSC 7 and a TA Instruments DSC 2920 with $N_2$ purging at a heating rate of 10–20° C./min. Some samples were tested on Mettler-Toledo DSC 822e at a heating and cooling rate of 20° C./min. Thermo mechanical analysis (TMA) tests were carried out on a Perkin-Elmer TMA 7 with He purging at a heating rate of 10° C./min. The liquid crystalline behavior of the compounds was studied using polarized microscopy (Nikon Eclipse E600) with crossed polarizers, equipped with a heating stage (Linkam THMS-600). The magnification used was 100 or 200×.

Synthesis of Polyesters: Bulk Polymerization

The monomers and approximately 500 ppm of KOAc were charged into a polymerization tube with a side branch. The system was degassed and purged with nitrogen three times. While purging with nitrogen, the temperature was increased to 250° C. for about 1.5 h, 280° C. for 30 min, 300° C. for 30 min, and 320° C. for 30 min. During the temperature gradient, acetic acid was collected in a test tube at the end of the side branch. At the final stage, while the reaction temperature was kept at 320–330° C., the side branch was sealed and vacuum was slowly conducted for 30–60 min to remove the acetic acid byproduct.

In most cases, the monomers melted at 220–230° C., and polymerization occurred with the evolution of acetic acid at around 250° C. After cooling to room temperature, the reaction vessel was broken and the resultant polymer was collected.

Synthesis of Polyesters: Non-Aqueous Dispersion Polymerization

In an 100 mL RB flask, the monomers (for an example, 0.612 g of CAPN, 0.540 g of ABA) and the catalyst (500 ppm) were mixed with dispersing agent, Ganex V-220 (0.045 g), and heat transfer oil, Therminol 66 (8.0 ml). The mixture was heated to 220–250° C. for about 2 h with $N_2$ purging and stirring. The temperature was then increased to 280° C. for 30 min, 300° C. for 30 min and 320° C. for 30 min.

After cooling to room temperature, the resultant polymer (powder solid) was isolated and extracted with hexane overnight and dried.

Inherent Viscosities of Polymers

Inherent viscosities (IV's) of polymers were measured in PFP/PFB mixed solution (w/w=1.46/1) at 30° C. with an Ubbelohde viscometer. The weighed polymer was dissolved in heated PFP. PFB was added and mixed completely. IV's were measured at a polymer concentration of approximately 0.2 g/dL in the mixed solvent system. The solution was filtered with a 1 μm filter before filling the viscometer.

Results and Discussion: Synthesis of Polyesters

Effect of Catalyst—KOAc and $Sn(OTf)_2$

For the polymerization, two different catalysts were studied with the model reaction of esterification of benzoic acid and phenyl acetate at 150° C. to compare their efficiency (Scheme 3.2). One catalyst is KOAc, which is commonly used in industry. The other is $Sn(OTf)_2$, is reported to be efficient for polymerization of lactones at low temperature. The concentration of the catalyst was 500 ppm. The two starting materials were charged into the flask at 1:1 ratio with the catalyst, and the reaction mixture was heated to 150° C. under stirring. The reaction was monitored by GC-MS at 1 hr, 2 hr and 4 hr.

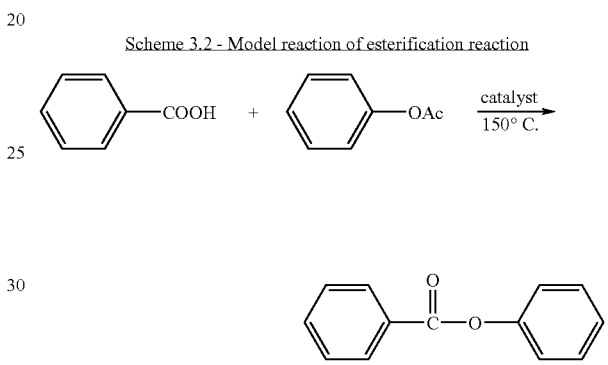

Scheme 3.2 - Model reaction of esterification reaction

The results from these two catalysts are listed in Table 8. After four hours, the product peak was still very small for the reaction that used KOAc as the catalyst. For the reaction using $(CF_3SO_3)_2Sn$ as the catalyst, the product peak was quite large after only one hour. After 4 hr at 150° C., conversion of starting materials to phenyl benzoate was greater than 95%. Therefore, the preliminary study demonstrated that $(CF_3SO_3)_2Sn$ is an effective catalyst for the acidolysis reaction and is effective at lower temperatures (150° C.) than the commonly used KOAc.

However, at higher temperatures (250° C., the starting polymerization temperature), it was difficult to operate the polymerization with the tin catalyst. The high activity of the tin catalyst at low temperatures causes premature homopolymerization of the lower melting monomer. 4-Acetoxybenzoic acid melts at 187° C. and 2-acetoxy-6-naphthoic acid melts at 228° C. Thus, melting of the lower melting point monomer in the presence of a catalyst active at low temperatures can induce significant homo-polymerization. Blocky structures can be formed and, in some cases, the melting points of the oligomers formed may increase beyond the polymerization temperature, causing solidification of the polymerization mixture. For the system using KOAc as the catalyst, significant polymerization began at around 250° C. At this temperature the starting materials are a well mixed solution. KOAc is easy to use in high temperature polymerizations and was used in subsequent polymerizations. However, the tin catalyst may be useful when used in lower concentrations.

TABLE 8

Catalyst effect for model reaction

| Catalyst | After 1 hour | After 2 hours | After 4 hours |
|---|---|---|---|
| No catalyst | Only starting material peaks | Only starting material peaks | Only starting material peaks |
| KOAc | Only starting material peaks | Small product peak $Area_p/Area_a = 0.006$ | Small product peak $Area_p/Area_a = 0.017$ |
| $(CF_3SO_3)_2Sn$ | Big product peak $Area_p/Area_a = 7.2$ | Big product peak $Area_p/Area_a = 13.7$ | Big product peak $Area_p/Area_a = 28.7$ |

$Area_p$: the peak area of product, M/Z = 198 (M$^+$)
$Area_a$: the peak area of benzoic acid, M/Z = 122 (M$^+$)

Polymerization Method

Two different polymerization methods were studied: bulk polymerization and non-aqueous dispersion polymerization.

(I) Bulk Polymerization Without Stirring

The bulk polymerization was conducted in a polymerization tube with a side branch. Usually monomers melted at 220–250° C. to form a clear yellow solution. Polymerization occurred around 250° C. and acetic acid distilled out of the reaction. Some sublimation of the monomer was observed at the beginning as the vapor condensed on the glass tube and the solid was washed down by the refluxing acetic acid. The bubbling action of the acetic acid helped with the mixing of the monomers. The polymerization tube was also shaken occasionally to ensure that a good mixture formed. For some compositions, the mixture solidified during the later stages of polymerization due to the high melting point of the products.

A Vectra-type LCP (HBA/HNA=58/42) were synthesized using this procedure as a control experiment. IV's as high as 5.1 were measured (usually the commercial VECTRA® has an IV around 5.0), which demonstrated that this method worked very well for this polymerization and produced high molecular polyester. IV's ranging from 1.8 to 6.7 dL/g were obtained for the soluble polymer compositions investigated in this thesis.

(II) Non-aqueous Dispersion Polymerization

Non-aqueous dispersion polymerization was also studied as a method to produce polyesters, with Therminol 66 synthetic heat transfer fluid as a dispersion medium. This is made from hydrogenated terphenyls and polyphenyls, and offers outstanding high-temperature performance up to 345° C. Ganex V-220 was used as a dispersing agent.

All of the starting materials were stirred and heated in a 3-necked round bottom flask. The mixture turned into a clear orange solution at approximately 250° C., and after 30–40 mins of polymerization, some powder began to participate from the solution and the mixture became cloudy. For some reactions, the polymer stuck to the magnetic stirring bar. The final product was usually a grey powder and was washed by hexane.

The TGA curves for the polymer showed two main weight losses. One of them was around 250° C., which indicated that the polymerization was not completed. One possible reason for this is that a vacuum stage was not used for this reaction and the complete removal of acetic acid needed even higher temperatures or longer times. DSC curves for the products were inconsistent, which may be caused by the incomplete removal of the heat transfer fluid or dispersing agent. Therefore, this method was not chosen for polymer synthesis.

Molecular Weight and Solubility of Polymers

Most of the synthesized polyesters are not soluble in any organic solvent, even hot pentafluorophenol (PFP). The best solubility was obtained from HNA/TA/DAPN co-polyesters. When the polyesters from this series had a melting point lower than 260° C., solubility in PFP/PFB mixed solvent was obtained. When the polymer had a higher melting point it was not soluble, although many polymers could still be swollen in heated pure PFP. The solubility of many polymers incorporating phenylene-naphthalene structures was lower than the commercial VECTRA® polymers. The majority of the polymers synthesized in this thesis were not soluble in hot PFP.

The inherent viscosity (IV) data for all soluble copolymers ranged from 1.8 to 6.7 dL/g, which is in the same range of VECTRA® polymers (approximately 3–5). This indicated that the polyesters were prepared with relatively high molecular weights. It was also found that higher IVs were obtained from A-B or B-A systems rather than the A-A or B-B systems, which was also true for VECTRA® polyesters. The stiochiometry is easier to control in A-B and B-A systems, which might be the reason for higher IV values. Alternatively, chain stiffness and the corresponding Mark-Houwink constants may vary in these systems, which would cause different IV values for the same molecular weights.

Thermal Properties of Polyesters

Polyesters from A-A Monomer

A-A monomer (DAPN) was copolymerized with HBA and TA to give a hard and brittle brown solid, which was not soluble in common solvents. The molar percentage of DAPN was between 15-30%. The thermal property results from the polyesters are listed below (Table 9). Most of the polymers were not soluble even in hot PFP, and the only soluble polymer (HBA/TA/DAPN=45/27.5/27.5) had an IV of 1.8 dL/g. One possible reason for its higher solubility may be the lower molecular weight, as indicated by the IV. The thermal stability for these polyesters was very good with most of the decomposition temperatures above 420° C.

TABLE 9

Properties of HBA/TA/DAPN copolyesters $$\left[\begin{array}{c}\text{OC}\phantom{xxx}\text{O}\end{array}\right]\phantom{x}\left[\begin{array}{c}\text{OC}\phantom{xxx}\text{CO}\end{array}\right]\phantom{x}\left[\begin{array}{c}\text{O}\phantom{xxx}\text{O}\end{array}\right]$$

| Sample ID | Composition HBA/TA/DAPN | IV[a] (dL/g) | 5% weight loss T(° C.) | 10% weight loss T(° C.) | Tg(° C.) | Tm(° C.) |
|---|---|---|---|---|---|---|
| Shao-01-120 | 75/15/15 | NS | 460 | 480 | — | 387 |
| Shao-01-109 | 60/20/20 | NS | 450 | 470 | — | 358 |
| Shao-01-67 | 50/25/25 | NS | 430 | 460 | 110~120 | 347 |
| Shao-02-58 | 45/27.5/27.5 | 1.8 | 420 | 440 | 115~120 | 353 |
| Shao-02-170 | 45/27.5/27.5 | NS | 439 | 455 | — | 351 |
| Shao-01-152 | 40/30/30 | NS | 420 | 460 | — | 346 |
| Shao-02-174 | 36/32/32 | NS | 407 | 442 | — | 352 |
| Shao-02-79 | 35/32.5/32.5 | NS | 415 | 435 | — | 372 |
| Shao-01-118 | 30/35/35 | NS | 450 | 480 | — | 390 |

[a]IV was obtained in pentaflorophenol and pentaflorobenzene mixture at 30° C.
[b]NS means not soluble in the mixed solvent The melting points (Tm) of this series of polymers were relatively high. The lowest melting point was above 340° C., which was obtained with 30% DAPN. Either increasing or decreasing DAPN from 30% will generate higher Tm for the copolymers. Glass transition temperatures (Tg) were not obvious on the DSC curves, and the shape of melting peak appeared quite similar to VECTRA® polymers, which was broad and small.

Some of the copolyesters were selected for annealing studies at 250° C. and 280° C. at different times. After annealing, the sample was retested by DSC. The results showed no significant change for these curves. The melting points shifted slightly to higher temperatures (less than 10° C.), and the shape looked slightly sharper. After annealing at higher temperature (280° C.), these effects became more pronounced. At longer annealing times, the melting peaks split into two clearly defined peaks, which indicated that the polymers have two different transition processes. Previous reports about VECTRA® polymers referred to these two transitions as slow transition and fast transition. It was also reported that the high melting peak remained at the same temperature, which was independent of annealing time while the low melting peak shifted to a higher temperature with increasing annealing time and the enthalpy increased as well. This was also true for the polyesters studied in this project.

Surprisingly, when the HBA monomer was replaced by HNA, the melting points of the polyesters dropped dramatically, to even lower than 240° C. (Table 10). The lowest melting point was obtained with 17% DAPN as co-monomer. Compared to the curve of HNA/TA/HQ, the minimum melting point is 50–60 degrees lower. Surprisingly, some low melting point compositions displayed sharp melting peaks. Furthermore, the solubility of the polyesters improved greatly and most of the compositions could be dissolved or swelled in the mixed solvent of PFP and PFB. Only polyesters having high DAPN composition (>30%) did not dissolve at all.

TABLE 10

Properties of HNA/TA/DAPN copolyesters $$\left[\begin{array}{c}\text{OC}\phantom{xxx}\text{O}\end{array}\right]\phantom{x}\left[\begin{array}{c}\text{OC}\phantom{xxx}\text{CO}\end{array}\right]\phantom{x}\left[\begin{array}{c}\text{O}\phantom{xxx}\text{O}\end{array}\right]$$

| Sample ID | Composition HNA/TA/DAPN | IV[a] (dL/g) | 5% weight loss T(° C.) | 10% weight loss T(° C.) | Tg(° C.) | Tm(° C.) |
|---|---|---|---|---|---|---|
| Shao-02-159 | 74/13/13 | Swells | 424 | 436 | 116 | 322 |
| Shao-02-146 | 70/15/15 | Swells | 418 | 431 | 111 | 307 |
| Shao-02-158 | 66/17/17 | 2.3 | 418 | 438 | 109 | 230 |
| Shao-02-145 | 60/20/20 | 3.4 | 416 | 432 | 112 | 233 |
| Shao-02-161 | 56/22/22 | 3 | 430 | 444 | 112 | 235 |
| Shao-02-144 | 50/25/25 | 2.9 | 420 | 435 | 113 | 259 |
| Shao-02-147 | 40/30/30 | NS[b] | 430 | 445 | 113 | 326 |
| Shao-02-149 | 30/35/35 | NS | 426 | 448 | 112 | 380 |

[a]IV was obtained in pentaflorophenol and pentaflorobenzene mixture at 30° C.
[b]NS means not soluble in the mixed solvent The thermostability for these polymers was high, with decomposition temperatures varying at only a narrow range for the different compositions (418–430° C.).

From the DSC curves, an obvious glass transition (Tg) can be observed at approximately 110–120° C., which is quite similar to the Tg of commercial VECTRA® (110–115° C.). The enthalpy change at the melting point was between 1.3–2.2 J/g. The obvious Tg transition indicated that compared to the HBA/TA/DAPN copolyesters, HNA/TA/DAPN copolyesters have a much higher percentage of amorphous structure. This is consistent with the higher solubility and lower melting points. All of this information suggests that HBA structure packs much better than HNA structure with the DAPN structure.

Polyesters from B-A Monomer

The B-A monomer (ACPN) was copolymerized with HBA or HNA, respectively. Similar to the previous series, the copolymers from HNA have much lower melting points than those of the HBA copolymers. The properties of HNA/ACPN copolyesters were summarized in Table 11. The compositions of ACPN were between 25–35 mol %, and most of the polymers have high decomposition temperatures (above 420° C.). Only one polymer was soluble in the mixed solvent of PFP/PFB, and an IV of 6.7 dL/g was obtained. This IV is much higher than the polymers from A-A monomer, possibly due to the better 1:1 stiochiometric ratio in A-B system than A-A/B-B system, thus producing higher molecular weight polymers.

The melting points of these polymers were between 260° C. to 350° C. The lowest melting point (~260° C.) was obtained with approximately 37 mol % ACPN monomer. Compared with the HNA/HBA curves, the shape of the melting point-composition curve is sharper, and the lowest melting point also shifted to lower compositions of ACPN%. The melting peaks shown on DSC curves were broad, similar to Vectra's melting peak. The average enthalpy change at Tm was around 2.8 J/g, which is larger than the previous series. Tg was not clearly detectable on the DSC curves.

The next series of polymers investigated were the HBA/ACPN copolyesters. The experiental data are shown in Table 12. Interesting DSC curves were obtained when the HNA monomer from the previous series was replaced by the HBA monomer. A large sharp endothermal peak was observed between 200–210° C. for the HBA/ACPN copolyesters. This peak appeared for most of the compositions, except for those with ACPN>80%. For ACPN=70%, the first endothermal peak was very small. Analysis by hot-stage microscopy showed that a fluid phase was not formed at these temperatures. In fact, changes in the sample could not be detected optically or by shearing the cover slip over the powdered sample.

TABLE 11

Properties of HNA/ACPN copolyesters

| Sample ID | Composition HNA/ACPN | IV[a] (dL/g) | 5% weight loss T(° C.) | 10% weight loss T(° C.) | Tg(° C.) | Tm(° C.) |
|---|---|---|---|---|---|---|
| Shao-02-137 | 75/25 | —[b] | 378 | 394 | — | 352 |
| Shao-02-105 | 70/30 | 6.7 | 425 | 438 | — | 268 |
| Shao-02-244 | 67.5/32.5 | NS[c] | 373 | 385 | — | 270 |
| Shao-02-115 | 65/35 | NS | 420 | 432 | — | 268 |
| Shao-02-107 | 60/40 | — | 426 | 440 | — | 260 |
| Shao-02-118 | 55/45 | — | 430 | 445 | — | 273 |
| Shao-02-109 | 50/50 | NS | 420 | 436 | — | 276 |
| Shao-02-110 | 40/60 | — | 425 | 438 | — | 301 |

[a]IV was obtained in pentaflorophenol and pentaflorobenzene mixture at 30° C.
[b]— means solubility was not attempted
[c]NS means not soluble

TABLE 12

Properties of HBA/ACPN copolyesters

| Sample ID | Composition HBA/ACPN | IV (dL/g) | 5% weight loss T(° C.) | 10% weight loss T(° C.) | Tg(° C.) | Tm(° C.) |
|---|---|---|---|---|---|---|
| Shao-02-88 | 70/30 | NS[a] | 395 | 408 | 214 | 391 |

TABLE 12-continued

Properties of HBA/ACPN copolyesters

[structure: –[–O–C(=O)–C6H4–O–]– and –[–O–C(=O)–naphthalene–C6H4–O–]–]

| Sample ID | Composition HBA/ACPN | IV (dL/g) | 5% weight loss T(° C.) | 10% weight loss T(° C.) | Tg(° C.) | Tm(° C.) |
|---|---|---|---|---|---|---|
| Shao-02-95 | 65/35 | —[b] | 415 | 425 | 208 | 386 |
| Shao-02-94 | 60/40 | — | 405 | 420 | 209 | 384 |
| Shao-02-89 | 50/50 | NS | 430 | 445 | 206 | 373 |
| Shao-02-263 | 45/55 | — | 345 | 380 | 198 | 363 |
| Shao-02-99 | 40/60 | — | 410 | 420 | 206 | 366 |
| Shao-02-265 | 30/70 | — | 380 | 408 | 195 | 353 |
| Shao-02-103 | 30/70 | — | 420 | 435 | 181 | 343 |
| Shao-02-266 | 25/75 | — | 390 | 411 | 197 | 357 |
| Shao-02-163 | 20/80 | — | 417 | 445 | — | 381 |
| Shao-02-181 | 10/90 | — | 428 | 452 | — | 383 |
| Shao-02-258 | 0/100 | — | 400 | 417 | — | 383 |

[a]NS means not soluble
[b]— means solubility was not attempted

After several tests by different techniques, such as x-ray, DSC and dielectric measurements, it was concluded that the transition was a crystal-crystal transition. It is obvious that this temperature is still far above the sharp endothermal peak temperature (200–220° C.) found in this work. At the low molecular end of the oligomers studies, the tetramer of HBA had a melting point of 260° C.

Since a Tg transition was not observed around 100–120° C., the possibility that the 200–210° C. peak represented the Tg was investigated. Wunderlich et al. have reported on hysteresis effects in polymer glasses that can lead to glass transition temperatures, which appear as endothermal "peaks" in the DSC curves. The appearance of the Tg is often a complex function of the thermal history of the polymer sample. Generally, the "peak" appearance results from a superheated glass that moves quickly toward equilibrium as soon as the time scale of the heating permits. DSC tests were performed at different heating rates for Shao-02-88, which had the composition of HBA/ACPN=70/30. As the heating rate decreased, the endothermal peak became decreasingly smaller. This behavior is consistent with hysteresis effects seen in polymer glasses at Tg.

This polyester was also heated to 400° C. and dropped immediately into dry ice. The quenched sample was checked by DSC test again at 10° C./min. Because of the rapid cooling rate, the polymer chains do not have time for better packing, and more amorphous phase forms. The quenched sample showed a typical Tg transition at around 200° C.

An annealing study for this polymer was also performed at 300° C. for 12 hours. After annealing, the first endothermal peak shifted slightly to lower temperature, and the entropy was smaller (ΔH=7.25 J/g→6.36 J/g) than the sample without annealing. Meanwhile, the melting peak became larger ((ΔH=2.8 J/g→4.1 J/g), as compared to the unannealed polymer. Annealing of other compositions gave similar results. The annealing usually increases the crystallinity of the polymer.

DMTA is a sensitive method to detect Tg transitions. The storage modulus will decrease and the loss factor, tan δ, will show a peak at the Tg transition. However, since the melting point for these copolyesters was around 400° C., it was difficult to make coherent film from hot pressing. A sample of thickness around 0.8–1 mm was obtained from hot pressing and subjected to TMA testing. The analysis was conducted in penetration mode under a static force of 50 mN at a heating rate of 10° C./min. There are two important results from this test. First, it is quite evident that there is not a Tg in the 100–120° C. range where most wholly aromatic polyesters show a Tg. Second, the penetration result seen at >200° C. is strongly indicative of the Tg.

A TMA expansion test was also conducted with a static force of 0 mN at a heating rate of 10° C./min. There are three different slopes on the curves. The initial slope is about $4 \times 10^{-3}$, and after the Tg transition (220–230° C.), the slope changed to approximately $1 \times 10^{-4}$. The final slope on the curve increased to about 0.8. These results are consistent with the current assignments of the Tg and Tm in the copolyester series.

In conclusion, a combination of thermal methods demonstrated that the sharp endothermal peak at approximately 210° C. is a Tg transition. The Tg transition temperatures from these methods were in good agreement with each other (200–230° C.). Most surprisingly, this Tg assignment is almost 100° C. higher than reported for other wholly aromatic polyesters.

A melting point-composition diagram for this series indicates that as the content of the ACPN monomer increased, the melting point of the copolyemers decreased, typical of the eutectic behavior observed in LC polyesters. However, the polyester melting points increased abruptly at ACPN concentrations above 70 mol % and remained constant at 383° C.

Polyesters from A-B Monomer

A-B monomer (CAPN) was copolymerized with HBA and HNA, respectively. Similar to the B-A monomer, the copolymers with HNA have much lower melting points than the HBA copolymers. The polyesters from HNA/CAPN have similar thermal properties to HNA/ACPN copolymers, i.e., a minimum melting point at approximately 260° C. (Table 13) with a CAPN composition around 35%. Compared with HNA/HBA copolymers, the shape of the curve is quite similar, and the only difference is that the minimum melting point was achieved with lower ACPN % than HBA %. Select samples were subjected to solubility testing, but were not soluble in hot PFP. Therefore, IV data was not obtained.

ACPN copolymers. It appears that hysteresis effects are also present in this series, and occasionally further complicated by relaxation effects near the Tg. As discussed previously,

TABLE 13

Properties of HNA/CAPN copolyesters

| Sample ID | Composition HBA/ACPN | IV | 5% weight loss T(° C.) | 10% weight loss T(° C.) | Tg(° C.) | Tm(° C.) |
|---|---|---|---|---|---|---|
| Shao-02-126 | 80/20 | NS[b] | 414 | 428 | — | 325 |
| Shao-02-133 | 75/25 | NS | 394 | 406 | — | 278 |
| Shao-02-120 | 70/30 | NS | 425 | 438 | ~115 | 264 |
| Shao-02-135 | 65/35 | —[a] | 400 | 414 | — | 249 |
| Shao-02-199 | 65/35 | — | 401 | 415 | — | 260 |
| Shao-02-203 | 63/37 | — | 390 | 412 | — | 270 |
| Shao-02-121 | 60/40 | NS | 414 | 424 | ~120 | 275 |
| Shao-02-201 | 60/40 | — | 393 | 412 | — | 267 |
| Shao-02-198 | 55/45 | — | 412 | 427 | — | 261 |
| Shao-02-207 | 55/45 | — | 388 | 408 | — | 267 |
| Shao-02-125 | 50/50 | NS | 418 | 433 | — | 287 |
| Shao-02-208 | 45/55 | — | 413 | 430 | ~115 | 293 |

[a] — means solubility was not attempted
[b] NS means not soluble

The Tg transitions were barely perceptible in the DSC curves, and the melting point peaks were broad and small. The enthalpy changes at the melting points were around 2.0–5.6 J/g, which is also very close to that of HNA/ACPN polymers.

Copolyesters from HBA/CAPN were also synthesized. Their compositions and properties were listed in Table 14. Solubility was very poor, therefore IV data was not obtained. This series of polymers produced some interesting DSC curves. Initially, the most prominent peak in the DSC curve appeared in the range of 175–210° C. The shape of the curve was similar to the shape of the DSC curves for the HBA/ACPN copolymers. It appears that hysteresis effects are also present in this series, and occasionally further complicated by relaxation effects near the Tg. As discussed previously, this behavior is a complex function of the previous thermal history on both heating and cooling conditions. When a faster heating rate (40° C./min) was used and the final temperature was increased to 460° C., a second endothermal peak appeared above 400° C., which is believed to be the melting point. The enthalpy change at the melting point was around 4.7–11.2 J/g, which is much higher than other series. Additionally, the Tg shape appeared similar to that described earlier for the HBA/ACPN series.

TABLE 14

Properties of HBA/CAPN copolyesters

| Sample ID | Composition HBA/CAPN | IV | 5% weight loss T(° C.) | 10% weight loss T(° C.) | Tg(° C.)? | Tm(° C.)[a] |
|---|---|---|---|---|---|---|
| Shao-02-250 | 80/20 | NS | 405 | 425 | 242 | 435 |
| Shao-02-74 | 70/30 | NS[c] | 420 | 435 | 210 | 440 |
| Shao-02-152 | 65/35 | —[b] | 426 | 430 | 189 | 430 |
| Shao-02-251 | 65/35 | — | 415 | 433 | 191 | 431 |
| Shao-02-156 | 55/45 | — | 409 | 424 | 163 | 417 |
| Shao-02-75 | 50/50 | NS | 450 | 460 | 160 | 420 |
| Shao-02-260 | 40/60 | — | 423 | 435 | — | 408 |
| Shao-02-267 | 30/70 | NS | 420 | 434 | — | 413 |
| Shao-02-270 | 20/80 | | | | | |

[a] Temperature was taken from DSC test at a heating rate of 40 ° C./min.
[b] means solubility was not attempted.
[c] NS means not soluble In summary, the polyesters from HBA/CAPN were quite similar to those from HBA/ACPN. One noticeable difference was the gradual shift in Tg with composition. The Tg shifts from 160° C. for the HBA/CAPN=50/50 composition to 242° C. for the 80/20 composition. A Tg shift of this magnitude has not been reported for wholly aromatic copolyesters. The melting points (420–440° C.) were much higher than those from HBA/ACPN.

Polyesters from B-B Monomer

The diacid monomer had very poor solubility and its melting point was much higher than other monomers (>350° C.). At 250–280° C., the monomer remained as a solid in the melted monomer mixture while the other monomers had already begun polymerization. As a result, only low molecular weight oligomers were produced.

Structure of Polyesters: Powder X-ray Patterns

The polyesters were ultrasonically treated to form a fine powder and x-ray spectra were taken at room temperature. Some of the polyesters showed very high degrees of crystallinity compared with VECTRA® (typical degree of crystallinity: 15–20%). Polyesters from HBA always gave higher degrees of crystallinity than those from HNA with similar composition, such as HBA/ACPN polyesters (40–45%,), HBA/CAPN polyesters (42–48%) and HBA/TA/DAPN polyesters (30–36%). When the HBA was replaced by HNA, the crystallinity decreased dramatically, such as HNA/CAPN (20–22%) and HNA/TA/DAPN (15–20%). Qualitatively, the differences can be observed since the more highly crystalline copolymers usually display several sharp peaks, while the less crystalline polymers display only a few peaks superimposed on an amorphous background. All of the data from x-ray was consistent with the previous DSC data and conclusions.

Liquid Crystal Behavior

The polyesters were studied under cross polarized microscope for their liquid crystal behavior and to confirm DSC results. Copolyesters from HNA/TA/DAPN have low melting points, thus were chosen for this investigation. The threaded texture did not disappear, even at 450° C. All of the polymers investigated in this thesis displayed similar textures and were consistent with classical nematic threaded textures.

In summary, different composition copolymers were synthesized successfully by copolymerization of TA, ABA or ANA with new phenylene-naphthalene monomers. The polymerization was carried out in bulk and at temperatures in the range of 250–330° C., and liquid crystalline polyesters with a relatively high molecular weight and thermal stability were obtained. The composition greatly affected the properties of polymers.

Solubility of these polymers was very poor. Only a small number of polymers could be dissolved in PFP/PFB solution. The IV's were between 1.8 and 6.7 dL/g. Polyesters from all hydroxy-acid monomer systems showed poorer solubility and higher IV than those from systems incorporating diols.

The diacetoxy monomer, DAPN, was copolymerized with HBA or HNA and TA. The HBA copolymers showed much higher degrees of crystallinity and melting points, and lower solubilities than the HNA copolymers. The HNA/TA/DAPN polyesters were found to have even lower melting points than the commercial VECTRA® compositions.

The A-B (CAPN) and B-A (ACPN) monomers were copolymerized with HBA or HNA. These two series of polymers showed similar properties. HBA copolymers showed unusually high Tg transitions which was confirmed by various TMA tests. HNA copolyesters showed much lower melting points than those of HBA copolyesters. The major difference between A-B and B-A series is the orientation of the ester bonds along the polymer chain. This also affected the polymer properties. For example, HBA/ACPN polymers showed a Tg at around 210° C., while the Tg's of HBA/CAPN polymers were 160–240° C. Their melting points and degrees of crystallinity were also quite different.

Some compositions showed degrees of crystallinity greater than 40%, which is very unusual for wholly aromatic LC polyesters. To our knowledge, these are some of the highest Tg's reported for wholly aromatic copolyesters to date.

In summary, the phenylene-naphthalene structure shows effects of lowering the melting points of polymers. Several series of polymers from HNA show even lower melting points than VECTRA® polymers. Also, some unexpected results were obtained, such as high Tg and high crystallinity of HBA copolymers.

Large Scale Synthesis of Copolyesters from A-A Monomer

As the HNA/TA/DAPN copolyesters provide the lowest melting points, and the monomer can be made from the least expensive starting materials, this composition was chosen for scale-up and fiber property evaluation. Monomers (HNA/TA/DAPN=60/20/20, 69.0 g of HNA, 16.6 g of TA and 32.0 g of DAPN) and catalyst KOAc (200~300 ppm) were charged into a 3-necked round bottom flask equipped with a mechanical stirrer, and a nitrogen inlet and outlet. The system was degassed and purged with $N_2$ three times. While stirring and purging with $N_2$, the temperature was increased to approximately 250° C. for 1.5–2 hours, 280° C. for 1 hr, 300° C. for 30 min. The vacuum was slowly introduced and lasted for 1–2 hr. When cooled to room temperature, the flask was broken and light brown hard solid was obtained.

Inherent viscosities (IV) of polymers were measured in a PFP/PFB (w/w=1.46/1) mixed solution at 30° C. with an Ubbelohde viscometer. The weighed polymer was dissolved in heated PFP first, and then PFB was added and mixed completely, with concentrations of approximately 0.2 g/dl. The solution was filtered with 1 µm filter before filling the viscometer.

Two batches of polyesters were synthesized in larger scale with the same composition (HNA/TA/DAPN=60/20/20). The first batch had a lower inherent viscosity (IV=3.0 dL/g), while the second batch experienced a longer time under vacuum at the final stage of the polymerization, and thus had a higher IV (3.9 dL/g).

Polyester Fibers

The granulated polymers were dried for several days. Before spinning, they were cold pressed into rods 4–7 cm in length and about 1 cm in diameter. Different spinning conditions were studied for both of the polymers. The results are listed in Table 15.

For Polyester I, the fiber broke occasionally when the Grid temperature was equal to or lower than 300° C. However, for grid temperature of 310° C. and 280° C. for pack temperature, stable fiber spinning was observed. The extrusion rate (through put) for most spinning trials was 0.3 cc/min. The fiber could be collected at 600–800 revolutions per minute (RPM) without substantial breaking of the fiber line. Therefore these optimized conditions were used for spinning polyester I.

TABLE 15

Spin Conditions for Polyester I*

| Spin # | Grid Temperature (° C.) | Pack Temperature (° C.) | Grid Pressure (psi) | Pack Pressure (psi) | RPM (meters/min) |
|---|---|---|---|---|---|
| 1 | 300 | 270 | 185 | 70 | 800 |
| 2 | 280 | 260 | 385 | 70 | 600 |
| 3 | 280 | 250 | 447 | 700 | 800 |
| 4 | 280 | 250 | 985 | 380 | 600 |
| 6 | 310 | 280 | 221 | 280 | 600 |
| 7 | 310 | 280 | 268 | 810 | 800 |

*Polyester I: HNA/TA/DAPN = 60/20/20, IV = 3.0 dL/g

For polyester II, the first and second spinning trials were not successful. Some un-meltable impurities blocked the hole and continuous fiber was not obtained. The granulated polymer particles were put into tetrachloroethylene, which has a density of 1.6 g/cm$^3$ and stirred, and allowed to stand for 10 minutes. The majority of the polymer particles were floating on the top of the solvent, and some pieces of glass were at the bottom of the solvent. The separated polymer was dried again before spinning.

Mechanical tests of the fibers were conducted at Ticona. All tests were conducted at 50% room humidity (RH) and at 23° C. The average denier was calculated from the weight of 10 or 15 cm fils per sample. 10 tests were conducted for each sample and the reported numbers were their average values. The gauge length was 10 inches.

Mechanical test data for polymer I is listed in Table 16. Most of the modulus values are around 610–640 g/denier, which are approximately the same as VECTRA® polymers (~600 g/denier). However, the break tenacity and break elongation were 3–5 g/denier and 0.7–0.9% respectively, somewhat lower than VECTRA® polymers (~10 g/denier and 1–2%). I-1 and I-7 had lower modulus values, and the test data were slightly more scattered, indicating that some of the single fibers were weak. Many factors can influence the tenacity and elongation-to-break values including impurities, spinning conditions, polymer molecular weight, etc. Although it is impossible to study all of the parameters in a limited number of spinning trials, we suspect that the molecular weight (IV) of this batch of polymers may be the major factor related to these values.

TABLE 16

Mechanical properties of single fiber (as spun)

| Spin Number | Denier[a] | Modulus (g/denier) | Break Tenacity (g/denier) | Break Elongation (%) |
|---|---|---|---|---|
| I-1 | 3.60 | 502.60 | 3.28 | 0.71 |
| I-2 | 3.00 | 631.90 | 4.27 | 0.72 |
| I-3 | 4.20 | 614.90 | 4.02 | 0.70 |
| I-4 | 4.80 | 524.60 | 3.70 | 0.76 |
| I-6 | 5.40 | 642.70 | 5.17 | 0.87 |
| I-7 | 4.80 | 483.40 | 3.32 | 0.73 |

[a] Denier: gram per 9000 meters

The results indicate that this polymer can be spun into good fibers with a grid temperature of 310° C. and a pack temperature of 280° C. The mechanical modulus of these fibers is similar to or slight higher than the VECTRA® polymers. However, the tenacity modulus and break elongation were lower.

The invention claimed is:

1. A liquid crystal polymer comprising at least one repeating unit selected from the group consisting of radicals of formula I, II, and IV:

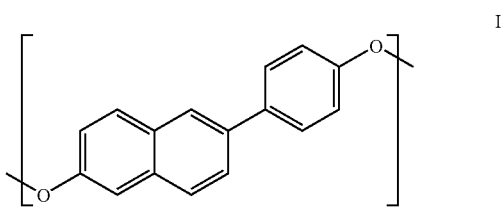

I

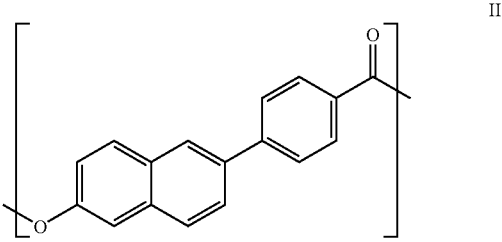

II

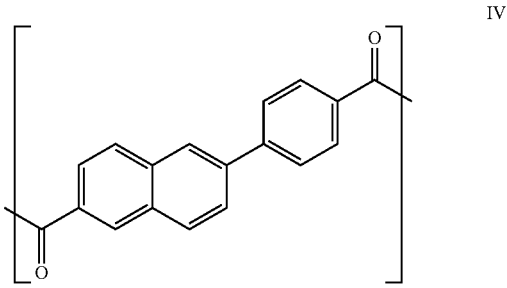

IV and combinations thereof.

2. An anhydrous liquid crystal polymer comprising at least one repeating unit selected from the group consisting of radicals of formula I, II, and IV:

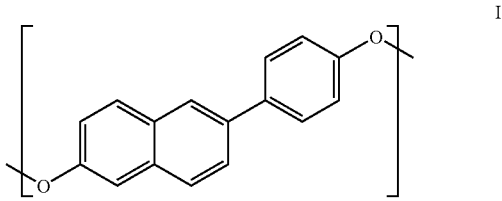

I

-continued

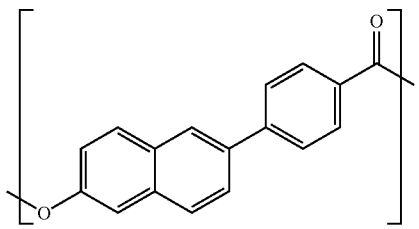
II

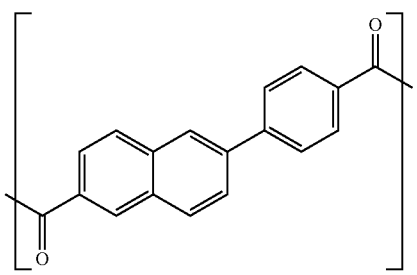
IV prepared by a process comprising thermally polymerizing a phenylene-naphthalene monomer selected from the group consisting of

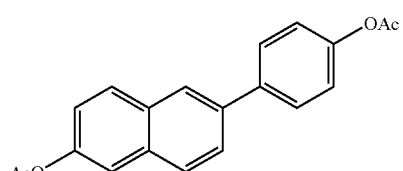

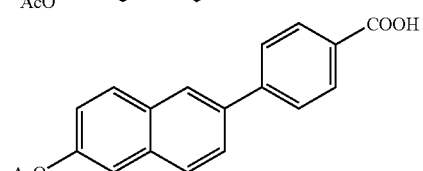

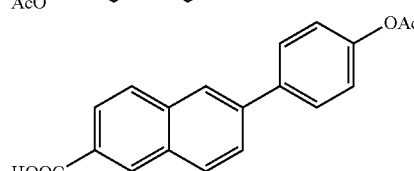

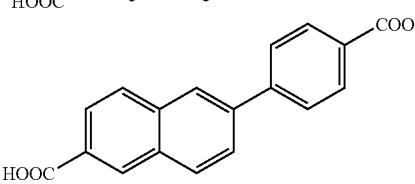

and combinations thereof, and, optionally, one or more comonomers.

3. A liquid crystal polymer according to claim 2, wherein said phenylene-naphthalene monomer is

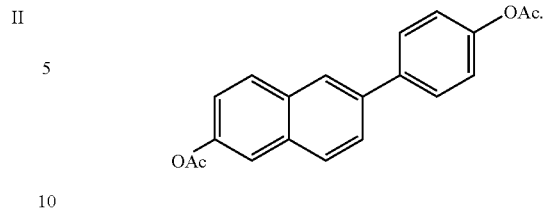

4. A liquid crystal polymer according to claim 2, wherein said phenylene-naphthalene monomer is

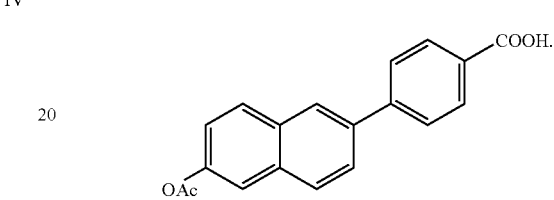

5. A liquid crystal polymer according to claim 2, wherein said phenylene-naphthalene monomer is

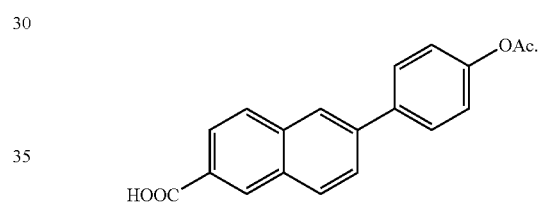

6. A liquid crystal polymer according to claim 2, wherein said phenylene-naphthalene monomer is

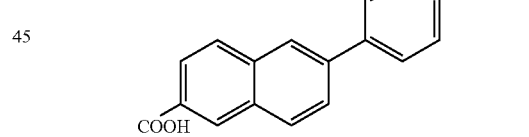

7. A liquid crystal polymer according to claim 2, wherein the one or more comonomers are selected from 4-hydroxybenzoic acid, 2-hydroxy-6-naphthoic acid, terephthalic acid, isophthalic acid, hydroquinone, derivatives thereof and combinations thereof.

8. A liquid crystal polymer according to claim 2, wherein the one or more comonomers is 4-hydroxybenzoic acid or derivatives thereof.

9. A liquid crystal polymer according to claim 2, wherein the one or more comonomers are 2-hydroxy-6-naphthoic acid or a derivative thereof.

10. A liquid crystal polymer according to claim 2, wherein the one or more comonomers are terephthalic acid or a derivative thereof.

11. A liquid crystal polymer according to claim 2, wherein the one or more comonomers are isophthalic acid or a derivative thereof.

12. A liquid crystal polymer according to claim 2, wherein the one or more comonomers are hydroquinone or a derivative thereof.

13. A liquid crystal polymer according to claim 1 or 2, comprising repeating units of formula

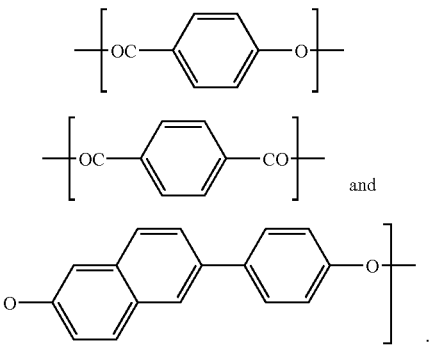

14. A liquid crystal polymer according to claim 1 or 2, comprising repeating units of formula

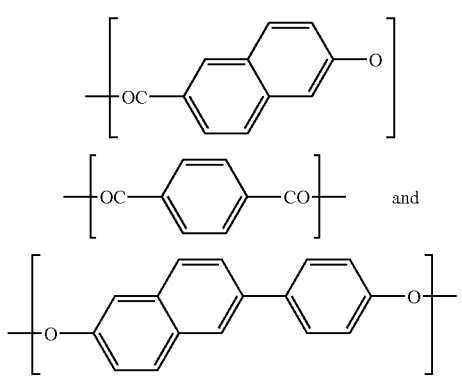

15. A liquid crystal polymer according to claim 2, comprising repeating units of formula

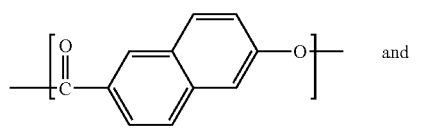

and

-continued

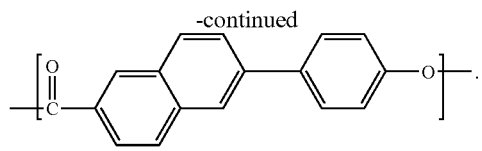

16. A liquid crystal polymer according to claim 2, comprising repeating units of formula

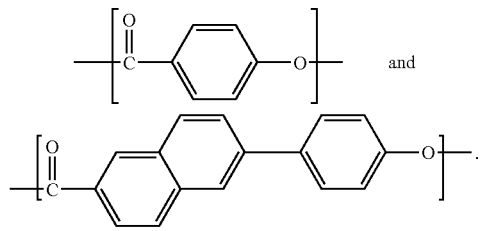

17. A liquid crystal polymer according to claim 1 or 2, comprising repeating units of formula

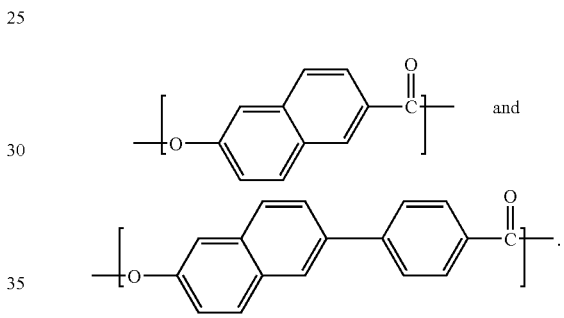

18. A liquid crystal polymer according to claim 1 or 2, comprising repeating units of formula

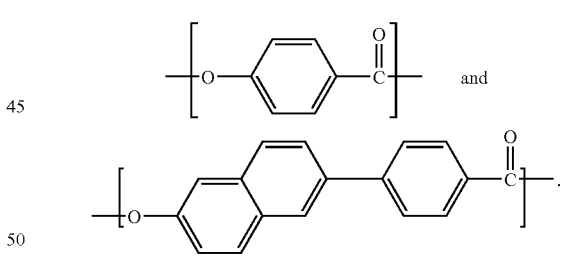

* * * * *